(12) United States Patent
Fenchel et al.

(10) Patent No.: US 8,848,997 B2
(45) Date of Patent: Sep. 30, 2014

(54) MEDICAL IMAGE ACQUISITION APPARATUS AND OPERATING METHOD THEREFOR

(75) Inventors: Matthias Fenchel, Erlangen (DE);
Andreas Schilling, Gomaringen (DE);
Stefan Thesen, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 671 days.

(21) Appl. No.: 12/498,535

(22) Filed: Jul. 7, 2009

(65) Prior Publication Data

US 2010/0002921 A1    Jan. 7, 2010

(30) Foreign Application Priority Data

Jul. 7, 2008 (DE) .................... 10 2008 032 006

(51) Int. Cl.
*G06K 9/00* (2006.01)
*G06T 7/00* (2006.01)
*A61B 5/055* (2006.01)
*G06F 19/00* (2011.01)
*G01R 33/54* (2006.01)

(52) U.S. Cl.
CPC ............ *A61B 5/055* (2013.01); *G01R 33/543* (2013.01); *G06R 19/3406* (2013.01); *G06T 2207/20081* (2013.01); *G06T 7/0026* (2013.01); *G06T 7/0034* (2013.01); *G06T 2207/10088* (2013.01); *G06T 7/0087* (2013.01); *G06T 7/0089* (2013.01); *G06T 7/0081* (2013.01); *G06F 19/321* (2013.01); *G06T 2207/20128* (2013.01); *G06T 7/0012* (2013.01); *G06T 2207/30004* (2013.01); *G01R 33/54* (2013.01)
USPC ........... 382/131; 382/128; 382/129; 382/130; 382/132

(58) Field of Classification Search
None
See application file for complete search history.

(56) References Cited

U.S. PATENT DOCUMENTS

| | | | | |
|---|---|---|---|---|
| 5,898,793 A | * | 4/1999 | Karron et al. ................. | 382/131 |
| 5,926,568 A | * | 7/1999 | Chaney et al. ................ | 382/217 |
| 5,946,425 A | * | 8/1999 | Bove et al. .................... | 382/294 |
| 7,167,760 B2 | * | 1/2007 | Dawant et al. ................ | 607/116 |
| 7,583,276 B1 | * | 9/2009 | Worthington ................. | 345/647 |
| 7,936,947 B1 | * | 5/2011 | Rueckert et al. .............. | 382/294 |
| 8,073,252 B2 | * | 12/2011 | Florin et al. .................. | 382/173 |
| RE43,282 E | * | 3/2012 | Alexander et al. ............ | 600/427 |
| 8,150,122 B2 | * | 4/2012 | Fenchel et al. ................ | 382/128 |
| 2005/0004617 A1 | * | 1/2005 | Dawant et al. ................. | 607/45 |

(Continued)

OTHER PUBLICATIONS

Rueckert et al ("Automatic construction of 3D statistical deformation models using non-rigid registration," In Medical Image Computing and Computer-Assisted Intervention 2001).*

(Continued)

*Primary Examiner* — Avinash J Yentrapati
(74) *Attorney, Agent, or Firm* — Schiff Hardin LLP

(57) ABSTRACT

In a medical image acquisition, and operating method, before acquiring a current planning image data set from a subject, a statistical atlas is generated from multiple planning image data sets using a specific measurement protocol, as a statistical compilation including an average image data set electronically associated with association information that identifies different anatomical entities represented by the statistical compilation. After the current planning image data set is acquired, the stored average image data set is transformed into the current planning image data set, with the association information being accurately associated with the current planning image data set. A diagnostic image acquisition of the subject is then controlled using the association information that is now associated with the current planning image data set.

29 Claims, 6 Drawing Sheets

(56) References Cited

U.S. PATENT DOCUMENTS

| | | | |
|---|---|---|---|
| 2005/0110791 A1* | 5/2005 | Krishnamoorthy et al. | 345/419 |
| 2006/0233430 A1* | 10/2006 | Kimura | 382/128 |
| 2007/0019846 A1* | 1/2007 | Bullitt et al. | 382/128 |
| 2007/0242865 A1* | 10/2007 | Fenchel et al. | 382/128 |
| 2007/0253611 A1* | 11/2007 | Rousson et al. | 382/128 |
| 2008/0159612 A1* | 7/2008 | Fu et al. | 382/131 |
| 2008/0253639 A1* | 10/2008 | Van Den Brink | 382/131 |
| 2009/0154783 A1* | 6/2009 | Bystrov et al. | 382/131 |
| 2009/0161820 A1* | 6/2009 | Raupach | 378/19 |
| 2009/0225077 A1* | 9/2009 | Sudarsky et al. | 345/423 |
| 2011/0007959 A1* | 1/2011 | Schulz et al. | 382/131 |
| 2011/0249876 A1* | 10/2011 | Dewaele | 382/128 |

OTHER PUBLICATIONS

Cootes et al ("Statistical Models of appearance for medical image analysis and computer vision", SPIE Medical Imaging, 2001).*

Fenchel et al ("Fully automatic liver scan planning-slice and navigator positioning from stacked 2D localizer scans", 2006).*

Park et al ("Spatial normalization of diffusion tensor MRI using multiple channels", 2003).*

"ON-Line Automatic Slice Positioning for Brain MR Imaging," van der Kouwe et al., NeuroImage, vol. 27 (2005) pp. 222-230.

Segmentation of the Prostate in MR images by Atlas Matching, Klein et al., IEEE from Nano to Macro. (2007) Apr. 12-15, 2007 pp. 1300-1303.

A Cross Validation Study of Deep Brain Stimulation Targeting: from Experts to Atlas-Based, Segmentation-Based and Automatic Registration Algorithms, Castro et al. IEEE Transact. on Medical Imaging, Vo. 25 No. 11 (Nov. 2006) pp. 1440-1450.

Automatic Construction of 3D Statistical Deformation Models Using Non-Rigid Registration, Rueckert et al. MICCAI (2001) Lecture Notes in Computer Science, vol. 2208, pp. 77-84.

"Construction of an Abdominal Probabilistic Atlas and its Application in Segmentation," Park et al. IEEE Trans Med, Imaging vol. 22 No. 4, Apr. 2003, pp. 483-492.

"Multiple Abdominal Organ Segmentation: An Atlas-Based Fuzzy Connectedness Approach," Zhou et al., Information Technology in Biomedicine, IEEE Transactions, vol. 11, No. 3 May 2007 pp. 348-352.

* cited by examiner

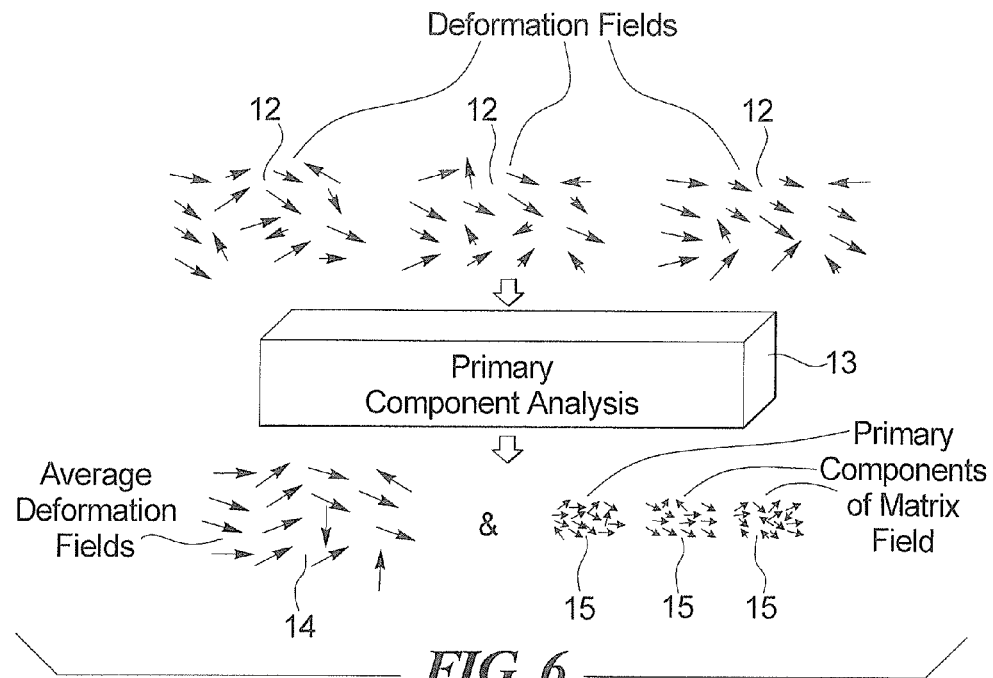
FIG. 6
FIG. 7
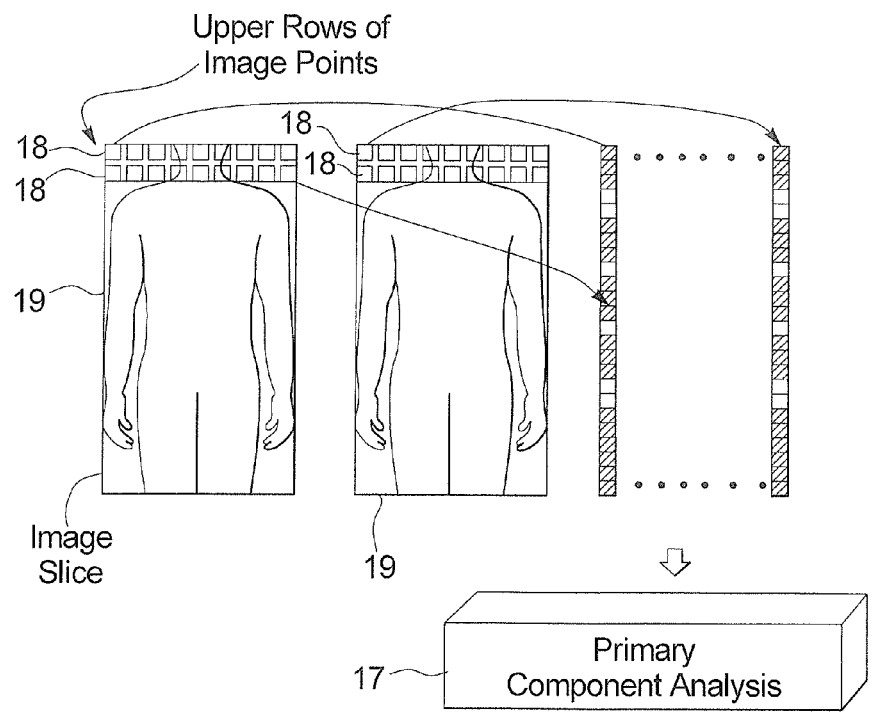

MEDICAL IMAGE ACQUISITION APPARATUS AND OPERATING METHOD THEREFOR

BACKGROUND OF THE INVENTION

1. Field of the Invention

The present invention concerns a method for controlling the image acquisition apparatus, as well as an image acquisition device, as well as an image acquisition device for implementing the method.

2. Description of the Prior Art

In order to be able to acquire qualitatively high-grade image data sets optimally suitable for a medical finding, not only does the acquisition region need to be determined with optimal precision but also other image acquisition parameters must also be adapted with regard to the patient or the type of examination. A large number of evaluation parameters are also required for a successful evaluation and preparation of the image data.

For this purpose, it is known to acquire planning image data sets, for example localizer image data sets in the case of magnetic resonance or low-dose planning image data sets in the case of computed tomography. The example of magnetic resonance will be discussed in detail, but similar problems also occur with other image acquisition modalities.

For diagnostic image acquisition with a magnetic resonance device, it is typical to initially acquire a localizer image data set. This is an image data set that can be acquired quickly due to special sequences, and typically such a localizer image data set shows large regions of a patient, or even the entire patient. The examination planning is conducted using these localizer image data sets. The localizers in particular serve to mark the volume of interest which, for example, contains an organ of interest, and to be able to correspondingly implement the slice planning. Additional parameters, in particular also patient-specific acquisition parameters, can be adapted by a trained operator from the localizer images.

The majority of these procedures today within the scope of the examination planning proceed manually. In the planning image data sets an operator must mark the volume of interest and, if necessary, additional regions of interest by hand, and must also set many acquisition parameters by hand. This results in the total time needed to acquire image data for the final (diagnostic) examination image data set that in all cases being lengthy, and non-standardized and cannot be reproduced.

A method for controlling the acquisition and/or evaluation operation of image data in medical examinations is known from DE 10 2006 017 932 A1. There it is proposed to use a statistical model of the target volume that is based on data about real anatomy, which model models a target volume (for example an organ) as a discrete polygonal mesh (thus geometrically). An average shape of the surface of the target volume is thus considered. This average shape should then be adapted to a shape determined from the planning image data set. This consequently deals with a position, orientation and shape of a special object, thus a geometric consideration.

DE 10 2007 019 514 A1 concerns a general framework for the image segmentation using ordered spatial dependency. This procedure is based on the recognition that structures can be more easily localized and identified when searches are conducted for their presence relative to other structures that are much easier to identify. Therefore the internal, structurally ordered spatial dependency should be used for a novel segmentation framework. The relative locations of the structures among one another are thus modeled.

Within the scope of minimally invasive procedures, segmentation and registration methods that use an atlas are known from the articles by S. Klein et al., "Segmentation of the prostrate in MR images by atlas matching", in: 4th IEEE Int. Symp. On Biomedical Imaging: From Nano to Macro, 2007, 12-15 Apr. 2007, P. 1300-1303, as well as by F. J. S. Castro et al., "A Cross Validation Study of Deep Brain Stimulation Targeting: From Experts to Atlas-Based, Segmentation-Based and Automatic Registration Algorithms" in: IEEE Trans. On Medical Imaging, Vol. 25, Iss. 11, November 2006, P. 1440-1450.

SUMMARY OF THE INVENTION

An object of the present invention is to provide a method that enables such examination planning (in particular with regard to the slice planning) to be largely automated, and to increase the image quality, standardization and reproducibility based on more exact definitions of acquisition parameters.

This object is achieved according to the invention by a method for controlling image acquisition in an image acquisition device, wherein a statistical atlas of at least one part of the human body is pre-generated before any part of a current examination. This statistical atlas includes an average image data set with association information regarding the anatomy (in particular organs) of the human body. This association information is associated with the respective image data from a number of planning image data sets acquired using a specific measurement protocol. A current planning image data set is acquired from the current examination subject. The association information; is automatically associated with the image data of the current planning image data set based on a transformation of the average image data set into the current planning image data set. The current image acquisition is implemented dependent on the association information of the current planning image data set.

The statistical atlas is used is specific to the measurement protocol for a number of subsequent image acquisition procedures for examination planning. For this purpose, a specific number of representative planning image data sets acquired with a specific measurement protocol are considered, such that as a result at least one average image data set exists at the end in which one item of association information was assigned to each image data point, this item of association information indicating which anatomical feature (for example an organ) corresponds to this image data point. This statistical atlas is stored in the image acquisition device.

If a special image acquisition should now be conducted with a specific patient, the acquisition of a current planning image data set thus initially ensues as is typical. In the simplest case, the measurement protocol that formed the basis of the planning image acquisitions used to generate the statistical atlas is also used to generate the current planning image data set. With an appropriate selection of the cost function for an optimization, other measurement protocols can also be used, in particular those that exhibit a similar contrast. This ensures the comparability of the current planning image data set with the average image data set. The goal is now to transfer the labeling of the average image data set that is defined by the association information to the current planning image data set so that the anatomy of the current patient (in particular the position of organs or other regions of interest) is precisely known. For this purpose, a transformation of the average image data set into the current planning image data set is determined. This involves registration of the atlas to the current planning image data set so as to correspondingly associate at least one image data point in the current planning image data set with every image data point of the average image data set that is provided with an item of association information. Thus the association information can simply be transferred to the current planning image data set. The image acquisition is controlled using this association information that is now also available for the current planning image data set. The method according to the invention offers many advantages.

The position of a region of interest that is to be acquired can be determined initially using the association information in the current planning image data set; corresponding acquisition parameters, in particular with regard to the slice position and/or the sequences, can be determined; and the image acquisition device can be correspondingly controlled. For example, in magnetic resonance acquisitions a navigator can also be positioned using the association information. Even a complete parameter optimization to the current patient, for example with regard to the fat saturation, the modeling of the calculation to specific absorption rates (sensor arrangement), the resolution in the examination image data set and additional parameters is conceivable, such that ultimately a fully automatic examination planning in the image acquisition region is enabled with the aid of the method according to the invention. This not only results in a simplification and acceleration of the examination, but also results in an increased reproduction capability of an image exposure due to the automatically implemented processes.

The image data evaluation can additionally be particularly advantageously controlled under consideration of the association information of the current planning image data set. It is additionally possible for the association information of the current planning image data set to also be taken into account in chronologically later additional examinations (follow-up examinations). With regard to the evaluation of the data of the examination image data set, for example, it is possible to conduct automatic pre-segmentations using the association information of the current planning image data set. In this context it is also possible to trim the examination image data set since the position of anatomical features in the patient is known using the association information with regard to the coordinate system of the image acquisition device, just like the position of the examination image data set in this coordinate system. Volumetric estimates can additionally be made from the association information. Assistance in the reporting with wholly automatic association of findings with regions or organs, automatic classification of examination image data sets for storage in databases, and labeling of examination image data sets for better orientation for the image evaluator are also possible. Correspondences can be automatically located in follow-up examinations. The association information can also serve as a starting point for location-specific organ-specific methods, for example an optimized positioning of various anatomical regions.

Through the wholly automated association of association information with image data points in the current planning image data sets, the method according to the invention thus makes a number of possibilities available that lead to an acceleration and simplification of the image acquisition in an image acquisition device as well as in the evaluation. A comparable image quality can additionally be achieved since, due to the automatic methods, a standardized and reproducible determination of parameters is enabled.

The method according to the invention can be particularly advantageously applied when the image acquisition device is a magnetic resonance device and the planning image data sets are localizer image data sets. Such three-dimensional localizer image data sets can be produced without great time delay in the workflow of magnetic resonance acquisitions and can serve in the method according to the invention as planning image data sets on which the statistical atlas is registered. However, use of the method according to the invention is also relevant for other image acquisition modalities. For example, the image acquisition device can be a computed tomography device and the planning image data sets can be low-dose planning image data sets. A low radiation dose is selected in order to not stress the patient but nevertheless to allow a planning image data set to be acquired that is suitable for examination planning.

To create the statistical atlas, the fundamental planning image data sets (in particular based on anatomical landmarks) can initially be translated into a common coordinate system. Such a first, rough registration of the planning image data sets simplifies the later determination of the average image data set. Landmarks as such are points of the anatomy that are simple to locate in many patients and are in particular selected manually or automatically. The consideration of edges, thus transitions from low to high contrast, is thereby particularly suitable, wherein bifurcations or points with high curvature can then be selected. Examples of this are the crotch, the nose, the chin or the like. The navel can also serve as a landmark.

It should be noted that it is generally useful to also conform the greyscale value distributions of the planning image data sets considered for generation of the atlas to one another since fluctuations can occur in spite of the use of the same measurement protocol. In order to achieve this, greyscale value histograms of all original planning image data sets can be generated, for example, wherein the position and width of specific maxima are the considered and shifted if necessary by scaling the original data. For example, this can occur in relation to a reference image data set.

A particularly advantageous procedure for generation of the statistical atlas is implemented by a reference image data set being selected from the planning image data sets, in particular based on high image quality, a mapping of every non-reference image data set to the reference image data set being determined, and the average image data set being determined, in particular by averaging all transformed planning image data sets and subsequent transformation with the inverse average map of all maps.

After selection of a reference image data set, all maps are accordingly determined that map the non-reference image data sets, or the individual image data points, to corresponding points of the reference image data set. Transformed non-reference image data sets and the reference image data set then exist that—when deformations are also taken into account—differ only in the greyscale values, but not structurally. To determine the average image data set, these are initially averaged into a greyscale value image data set. All maps are likewise averaged, such that an average map results. Since the reference image data set was selected arbitrarily or using quality criteria, it thus does not contain a representative average, but rather represents a bias. This allows the average image data set to be determined via transformation of the greyscale value image data set with the inverse average map in order to obtain a statistical atlas independent of the reference image data set.

The maps can particularly advantageously comprise an affine map and a deformation map, in particular an addition of an affine map to a deformation map. Affine transformations such as displacements, size changes and the like are taken into account, as well as deformations. A much more precise average image data set can therefore be determined. In particular, the deformation map can be represented by a vector field grid (lattice), wherein an interpolation can ensue via a B-spline tensor (advantageously of the third order). B-spline deformations are particularly well suited because they unify the advantages of smoothness and the local limitation of their parameters with one another. According to the invention, a grid is thus placed over the image data of the planning image data sets that are used, wherein the grid points described by the vector field [grid] can be shifted. This procedure to determine the mapping can proceed (in particular hierarchically) under step-by-step increase of the resolution of the vector field grid in order to be able to more quickly approximate the solution in this way.

In another embodiment of the method according to the invention, not only is the average image data set considered, but also the scattering of the planning image data sets around this average data set. For this purpose, in addition to the average map, the covariance of the map is also determined. This is in particular advantageously applicable to the effect that, after removing affine portions from the covariance by means of a primary component analysis, an average deformation and the primary components of the deformation (in particular with their eigenvalues) can be determined. The primary components of the deformation and their eigenvalues can advantageously be used in the later determination of the transformation into the current planning image data set. It is thus possible for at least a portion of the primary components, which is determined using the magnitude of the eigenvalues, to be taken into account in the determination of the deformation ratio of the transformation into the current planning image data set. In the abstract sense, the primary components represent directions in which variances of the deformations from the average deformation exist in the registrations of the planning image data set, wherein their importance results from the magnitude of the eigenvalue. All valid instances of the linear space of the input deformation fields (thus ultimately of the linear space of the planning image data sets used to generate the statistical atlas) can be generated from the primary components via linear combination. However, the information of along which primary component deviations are frequently or strongly present can advantageously be taken into account in the search for the transformation of the average image data set into the current planning image data set, in that predominantly transformations preferring this direction are taken into account, in particular within the scope of an optimization method. For example, the 20 primary components with the highest eigenvalues can be taken into account. Another possibility is to determine and take into account the magnitudes of the primary components or linear coefficients. These are taken into account given a limitation of the parameters of the deformation portion of the transformation into the current planning image data set, thus in the later registration with the atlas. For example, a maximum allowable deviation from three times the value of the standard deviation or variance (the eigenvalue) can be assumed.

Similar considerations can be made with regard to the greyscale values. An average greyscale value image data set and an associated per-pixel greyscale value covariance are determined if a conformation of the greyscale value distributions of the planning image data sets accounted for to generate the atlas ensues in advance as described above. It also is possible for the primary components (in particular with their eigenvalues) to be determined from the greyscale value covariance by means of a primary component analysis. Like the primary components of the deformation covariance, these primary components are then advantageously usable in the registration in the event that the transformation into the current planning image data set (which transformation is determined later in the registration) also contains a greyscale value portion. In this case, at least one part of the primary components of the greyscale value variable (which part is in particular determined using the magnitude of the eigenvalues) is taken into account in the determination of a greyscale value portion of the transformation into the current planning image data set. Here it has proven to be useful to select the ten primary components whose eigenvalues have the highest magnitude. Alternatively or additionally, it is possible for—given determination of the linear coefficients—the eigenvalues to be taken into account given a limitation of the parameters of a greyscale value portion of the transformation into the current planning image data set. For example, a limit can also be set here at three times the standard deviation.

In general, the determination of the maps (thus the registration transformations for the generation of the atlas) can ensue in an optimization method. Such optimization methods are known and are generally based on the identification of a minimum or maximum for a cost function. Normalized mutual information (NMI) and/or the smoothness of a deformation vector field and/or the quality of the correspondence of marked landmarks can be taken into account in the cost function. While it is frequently typical to consider the sum of the of the interval squares, according to the invention normalized mutual information (NMI) is used. The reason for this is that an equal distribution of greyscale values in different patients frequently does not exist directly; for example, identical structures in different patients exhibit strongly different intensities. Therefore, to determine the optimal mapping in the present case it is more advantageous to use comparison measurements that are based on a common histogram of both images, wherein a measurement based on entropy is used as mutual information in the common histogram. In accordance with the invention, the mutual information is normalized with regard to an overlap between the image data, thus the generally known normalized mutual information (NMI) is used. In addition, a term can be used that describes the smoothness of a deformation vector field (see above in this regard) since deformations that describe anatomical features for the most part locally change only slightly. It is likewise possible to use a term in the cost function that pertains to the correspondence of marked landmarks, for example those that were used to translate the planning image data sets into a common coordinate system.

In particular, in addition to an hierarchical determination of the mappings (thus registration transformations) with step-by-step increasing of the resolution of the vector field grid, it can be provided that the determination of the maps ensues hierarchically with step-by-step increasing of the resolution of the presently considered planning image data set, in particular in the manner of a Gaussian pyramid. Given this procedure the low-pass filtering is realized by aliasing with a Gaussian bell. Given use of two hierarchies, a priority order between these thereby does not need to exist; for example, the image resolution and the grid resolution can be increased in alternation. In this way the optimal solution is approached effectively and while circumventing local minima or, respectively, maxima of the cost function. The hierarchy can in particular be selected in the manner of a Gaussian pyramid such that, for example, three resolution levels are provided at which the resolution is increased.

An association of association information with regard to the anatomy of the human body with the image data ensues to conclude the generation of the statistical atlas. For this purpose, the association information regarding anatomy of the human body are associated manually and/or automatically (in particular semi-automatically by means of a segmentation method) with the image data of the average image data set. Semi-automatic methods in particular have proven to be advantageous here, in which methods an experienced assessor of magnetic resonance exposures predetermines seed points for specific organs or structures or initially defines their edges, for example, from which the general labeling (thus the association information) can be derived from known segmentation algorithms. Naturally, however, entirely manual or entirely automatic methods are also suitable. Marking the anatomy of the human body is in principle naturally also already possible in the reference image data set, since this is then directly transformed into the atlas anyway via the average map.

The statistical atlas is therefore created that, for example, can be stored in a control device or computer of the magnetic resonance device and can serve for evaluation of various currently acquired planning image data sets. As described above, in addition to this the determination of a transformation is provided that allows the assignment of association information (thus a labeling) in the current planning image data set. For this it is again initially reasonable to conduct a greyscale value conformation as described above. For example, it is reasonable when the current planning image data set is acquired with the same measurement protocol as the planning image exposures forming the basis of the generation of the atlas.

The transformation into the current planning image data set can be determined using an optimization method. A gradient downscaling method with adaptive interval [step] width or a Gauss-Newton method can thereby be used. In the Gauss-Newton method the function evaluation ensues in disjoint blocks distributed across the image data set. The calculation of the gradients can ensue numerically via symmetric differences. The interval width for the calculation of the gradients can be selected individually for each parameter. It is generally advantageous for the transformation to have an affine portion and a deformation portion, in particular like the maps determined in the generation of the statistical atlas. It can additionally be advantageously provided that the transformation determined upon registration with the atlas also comprises a greyscale value portion. For the parameters pertaining to the affine portion and the deformation portion, the interval width can then be predetermined so that an image data point is displaced by a maximum of the dimension of one voxel. For the parameters of the greyscale value portion, the step interval can be predetermined so that the greyscale values vary by 15% of the maximum possible greyscale values, thus for example by 38 given 256 greyscale values. Naturally, it is also possible to make the interval width dependent on other variables, for example on a scattering in the greyscale value histogram or on eigenvalues determined within the scope of a primary component analysis of a variance field for the statistical atlas, as was already discussed in the preceding.

The sum of the interval squares or of the weighted interval squares can presently be selected as a cost function for the optimization in the determination of the transformation; however other cost functions are also possible.

The advantageous possibilities to control the image acquisition and possibly also the image evaluation have already been discussed in detail in the description of the prior art.

In particular the aspects of the method according to the invention concerning the determination of the transformation into the current planning image data set require a certain computing time that should be kept optimally short in order to be able to apply the method to an image acquisition device in practice. In an embodiment of the method according to the invention, therefore, at least one part of the calculations for determination of the transformation into the current planning image data set is in particular parallelized by the GPU (graphics processing unit) of a graphics card. The texture memory of the graphics card can thereby also be advantageously used, which allows a faster access to image data. In recent times GPUs have been increasingly optimized with regard to such parallel floating point operations, primarily due to rising demands by computer games. Matrix multiplications and the like can therefore be implemented on graphics cards much faster than on the CPU (central processing unit) of a computer that must be designed with regard to a plurality of additional optimization criteria and offers only very limited possibilities for parallel calculation. Modern graphics cards now offer access to powerful and, most of all, parallelizable floating point calculation resources via programmable shaders. Therefore the implementation of the cited portion of the method according to the invention that is proposed according to the invention is therefore possible in a fragment shader program capable of being run on a GPU, wherein the compatibility with graphics card hardware available in the image acquisition device is taken into account. The performance is advantageously enormously increased via the execution on the GPU, to which the use of the texture memory also contributes. In an exemplary implementation of the method according to the invention, an acceleration by a factor of 500 was achieved. The running time to determine a transformation within the scope of the registration with the atlas \is thereby in the range of approximately 10 seconds. The daily use of the method according to the invention can therefore easily be realized.

Primarily the data transfers from main memory to the graphics card can represent a problem with the use of a GPU. Therefore, in a further embodiment of the method according to the invention it can be provided that all calculations on the image data are conducted by the GPU except for the calculations pertaining to an optimization. Large data sets (for example of a deformation field) therefore do not have to be transferred since, for example, the multiplication of the primary components with the weighting parameters can be calculated just as well on the graphics card as the greyscale value distribution in the atlas, the comparison of the images and the calculation of the cost function. "Bottlenecks" are therefore prevented since the upload and download to and from the graphics card are limited to a minimum of a few scalar values (affine parameters, weighting parameters) and the return transfer of the scalar values of the cost function.

In addition to the method according to the invention, the present invention also encompasses an image acquisition device that is fashioned for implementation of the method according to the invention. All embodiments of the method according to the invention are applicable to the image acquisition device, which thus embodies a tool in order to improve and accelerate the examination planning and possibly also the image evaluation.

In particular, such an image acquisition device can have a computer and a graphics card with multiple programmable shaders, wherein the graphics card can be fashioned to implement at least one portion of the calculations to determine the transformation into the current planning image data set in a parallelized form, in particular to implement all calculations on the image data except for the calculations pertaining to an optimization.

BRIEF DESCRIPTION OF THE DRAWINGS

FIG. 6 is a basic diagram of the primary component analysis of a deformation variance field, FIG. 7 is a representation of the per-pixel primary component analysis with regard to the greyscale values.

DESCRIPTION OF THE PREFERRED EMBODIMENTS

The method according to the invention embodies two portions that can separated from one another in time. A statistical atlas is initially created that should be suitable for a number of automatic examination plannings and executions ensuing in the second section. Even though the exemplary embodiment is explained in the following for a magnetic resonance device, the application of the method according to the invention to other image acquisition devices (for example a computed tomography device) is also possible.

Figure 1:
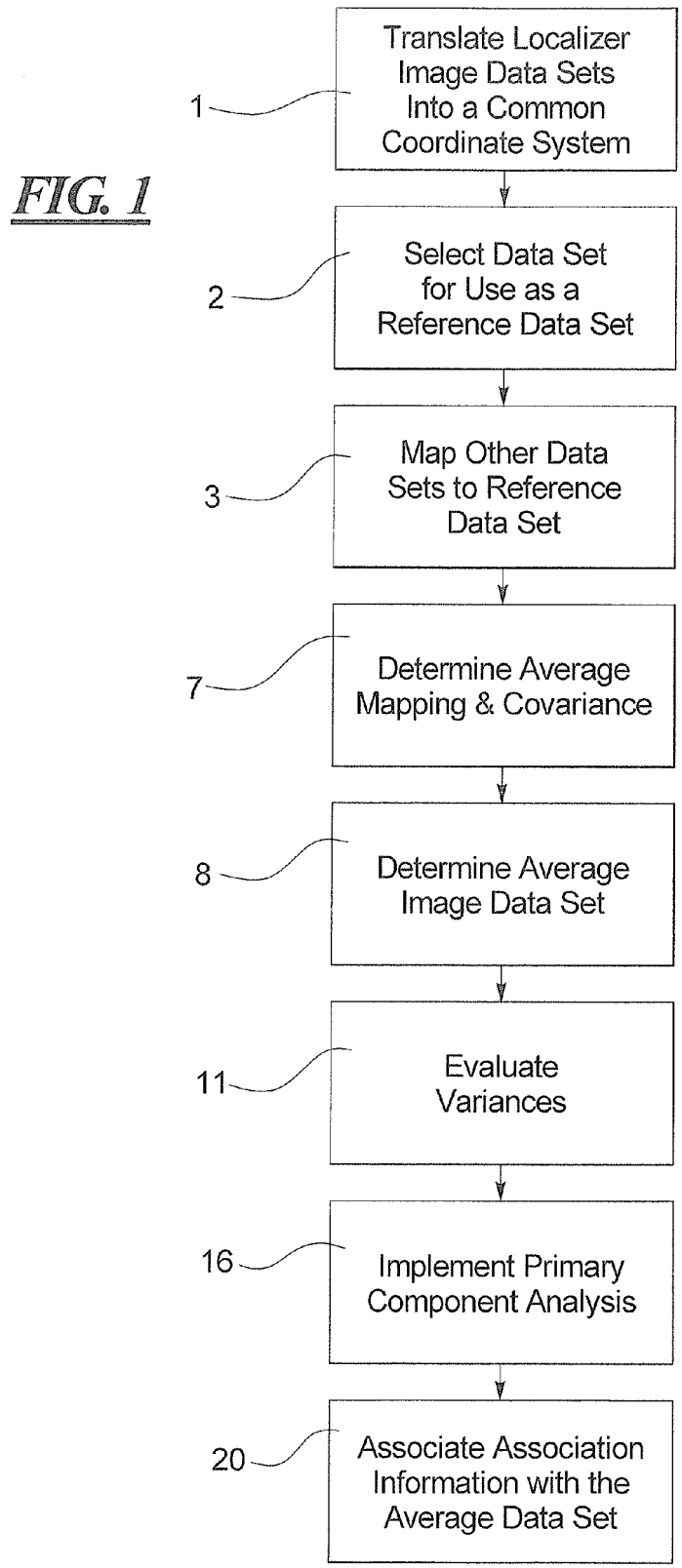
FIG. 1 is a flowchart to generate a statistical atlas within the scope of the method according to the invention.

FIG. 1 shows a flowchart for the creation of a statistical atlas within the scope of the method according to the invention. First, a plurality of localizer image data sets acquired with a specific measurement protocol is translated into a common coordinate system in Step 1, and a greyscale value conformation is conducted. For this anatomical landmarks are initially marked manually or via a corresponding algorithm in each of the localizer image data sets. For example, these can be the chin, the nose, the crotch and/or the navel of the respective patient. The images are registered with one another based on these anatomical landmarks, thus are translated into a common coordinate system. For greyscale value conformation, the greyscale value histograms of the individual localizer image data sets are examined, in particular for significant maxima that are then scaled as necessary so that they lie at the same greyscale values for all localizer image data sets. However, other types of greyscale value conformation are also possible.

In Step 2 a reference image data set is then arbitrarily selected from the localizer image data sets. In an ideal case it is not relevant how the selection occurs, since a bias generated by the choice of the reference image data set is removed again anyway in the course of the method, as will be shown below.

Figure 2:
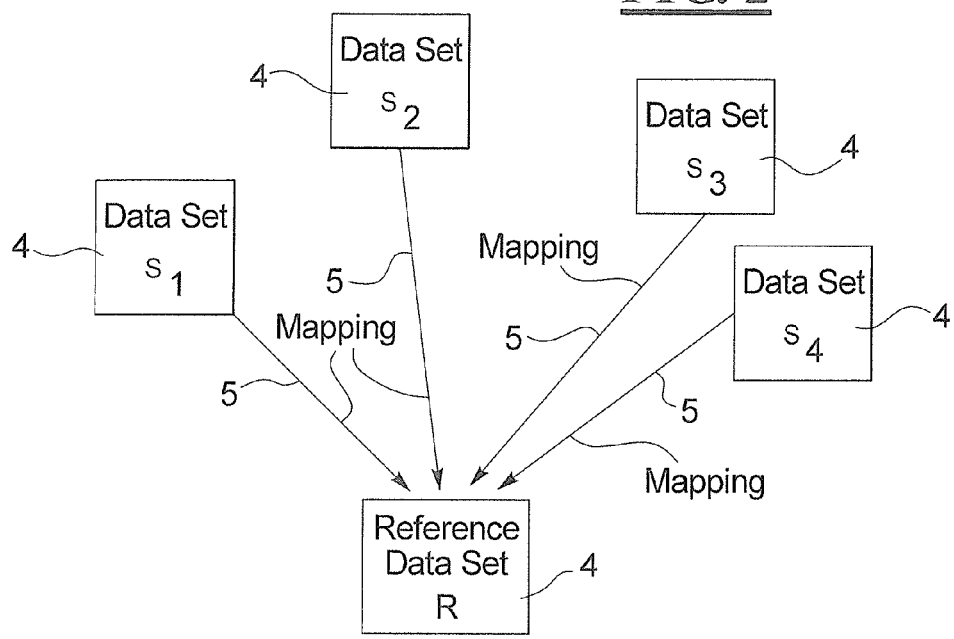
FIG. 2 is a basic diagram of the determination of mappings to a reference image data set.

In Step 3, mappings for each non-reference image data set to the reference image data set are determined. This is explained in detail via FIG. 2. There multiple localizer image data sets 4 forming the basis of the statistical atlas are shown. A reference image data set R has been selected from these. For each remaining localizer image data set 4 (thus non-reference image data set) marked with $s_1$-$s_4$ in FIG. 2, a mapping 5 is then determined that associates at least one image data point in the reference image data set R with every image data point of a non-ref image data set $s_1$.

Figure 3:
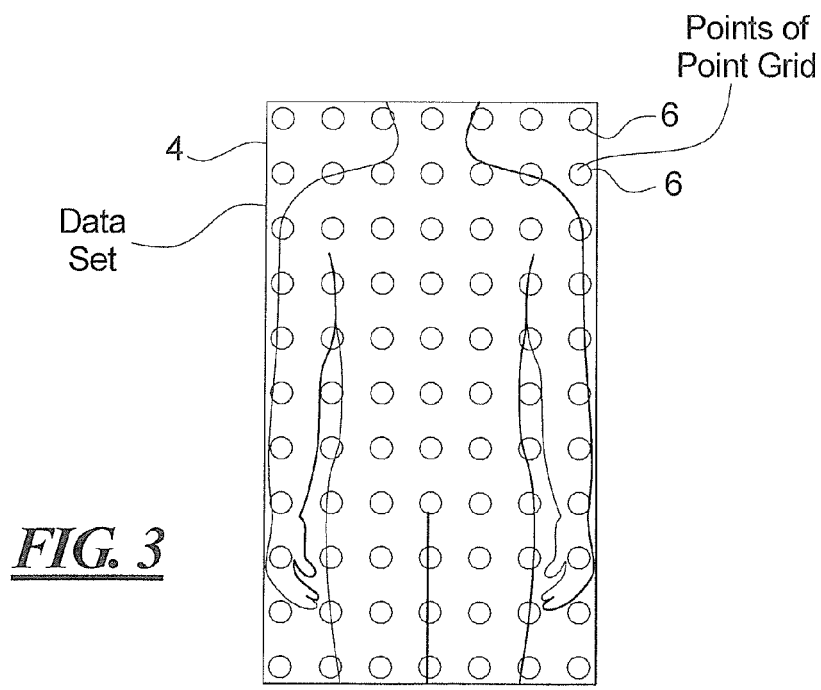
FIG. 3 illustrates a vector field grid placed over image data.
Figure 4:
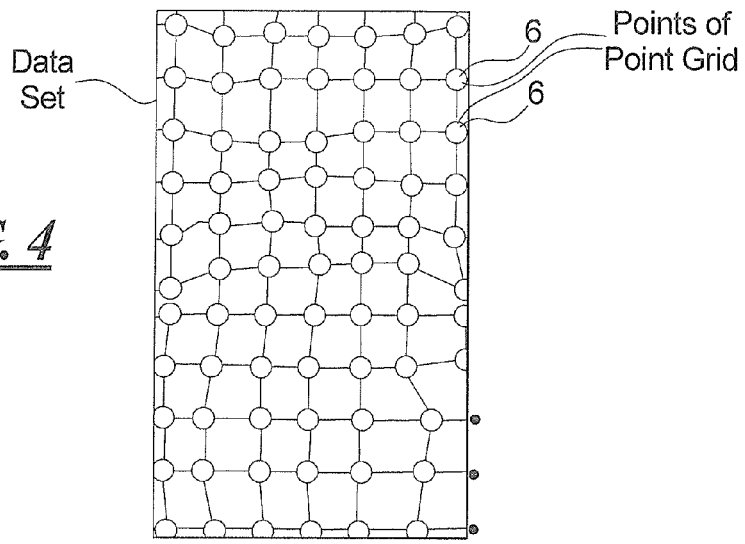
FIG. 4 shows an example of a smooth deformation vector field.

This presently occurs within the scope of an optimization method. Various optimization methods sufficiently known in the prior art can thereby be used. A sum of an affine mapping and a deformation mapping is selected as a basic form. The deformation mapping is thereby represented by a regular vector field grid interpolated with a B-spline tensor of the third order. This is explained in detail through FIGS. 3 and 4. FIG. 3 shows a section through a localizer image data set 4 over which a point grid with individual points 6 has been laid. In an optimization step, each of the points 5 can now be shifted in a specific direction, as shown in FIG. 4. The displacement vectors by which the points 6 are shifted thereby form what is known as the vector field grid. In the optimized state, such a vector field grid is then obtained for each localizer image data set 4. More detail for the determination of a mapping in this way can be learned from, for example, the article "Automatic construction of 3D statistical deformation models using non-rigid registration" by D. Rueckert, A. F. Frangi and J. A. Schnabel, published in MICCAI 2001, which is herewith incorporated in its entirety into the present disclosure.

The optimization proceeds hierarchically twice, wherein first the resolution of the vector field grid is increased step-by-step; and then the image data sets are first registered in low resolution in the manner of a Gaussian pyramid in order to then proceed to higher resolutions. A step within the hierarchy is always conducted in alternation, meaning that first the process proceeds to the next higher resolution, then the resolution of the grid is increased, then the next higher resolution is selected again, etc. Three levels are thereby provided within the Gaussian pyramid, wherein it begins at one quarter of the original resolution. The resolution of the grid is increased until a grid point finally falls at every n-th (in particular every second) image data point.

Three terms are presently considered in the cost function for the optimization. Use of the normalized mutual information (NMI) is suitable for this. This forms the comparison measurement or the metric for the optimization of the mapping. Terms for the smoothness of the vector field as well as for the quality of the correspondence of landmarks marked in Step 1 are additionally provided. The two cited additional terms can thereby be provided with weighting factors.

An average mapping is then determined from the individual mappings in Step 7 (FIG. 1). A covariance of the mappings is also additionally determined in Step 7. The mappings are thus statistically evaluated.

Figure 5:
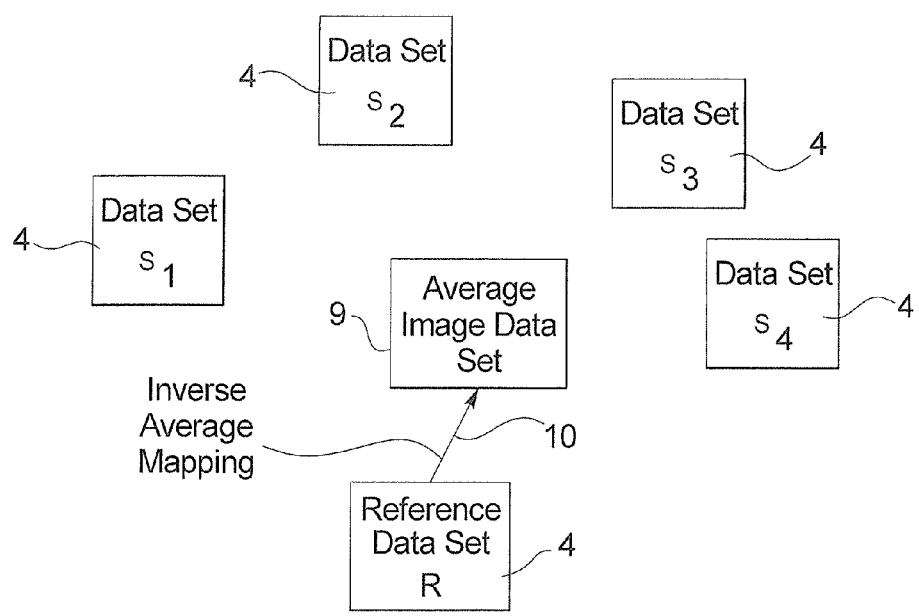
FIG. 5 is a basic diagram of the determination of the average image data set.

In Step 8, an average image data set 9 is then determined from the reference image data set R via transformation of a greyscale value image data set (calculated from the averaging of the transformed non-reference image data sets and the reference image data set, which thus differ merely in the greyscale values) with the inverse average mapping as it was determined in Step 7, as is schematically shown in FIG. 5. The arrow 10 therein designates the inverse average mapping. Effects due to the selection of the reference image data set R are eliminated in this manner.

After the average image data set 9 has been determined in this way, the evaluation of the variances (likewise determined in Step 7) now follows in Step 11. A deformation covariance that represents the variances of the various determined deformation fields as they are shown by way of example in the reference characters 12 in FIG. 6 is initially calculated with the removal of the affine portion. Moreover, it is also possible to directly determine the deformation covariance from the deformation fields 12 while circumventing the affine portions. The deformation covariance is now subjected to a primary component analysis 13 in Step 11. The resulting linear model can be expressed mathematically as follows:

$$d = \bar{d} + P*b,$$

wherein d is a deformation field, $\bar{d}$ is the average deformation field (which is represented with the reference character 14 in FIG. 6) and P is a matrix that contains the primary components indicated with 15 in FIG. 6 as columns, b is a weighting factor that reflects the proportions of the respective primary components 15 in the deformation field d.

Within the scope of the primary component analysis 13, the eigenvalues associated with the primary components are simultaneously determined. By their magnitude these indicate the importance of the respective primary components. The determined primary components 15 and the eigenvalues are stored with the average image data set in the statistical atlas.

In an optional Step 16, FIG. 1, it is possible to also conduct a primary component analysis 17 for the greyscale value distribution, shown in principle by FIG. 7. The deviations of the greyscale values from the average image data set are thereby considered for every image data point of the localizer image data sets 4, wherein these are respectively presently considered as a column vector of the individual rows, as is schematically represented above in FIG. 7 at the two upper rows 18 for two different slices 19 of an image data set 4. An average greyscale value deviation as well as a corresponding covariance can also be determined from these, from which the primary components with their eigenvalues can be determined in a known manner. These are also stored in the statistical atlas.

The association of association information with the image data of the average image data set now ensues in Step 20. This presently occurs semi-automatically in that an experienced expert marks the position of anatomical features (in particular of organs and structures) via encircling or via selection of seed points, after which the corresponding organs and structures are completely determined via corresponding segmentation algorithms. Information regarding which organ or which structure belongs to the corresponding image data point in the average image data set is then associated with the image data.

The generation of the anatomical atlas is concluded with Step 20, which anatomical atlas is stored in a computer of a magnetic resonance device.

It is again emphasized that, except for the possible manual marking of the landmarks in Step 1 (which, however, can also ensue automatically), all Steps can be implemented automatically; in particular, the statistical atlas can also be generated in a completely automated manner.

Figure 8:
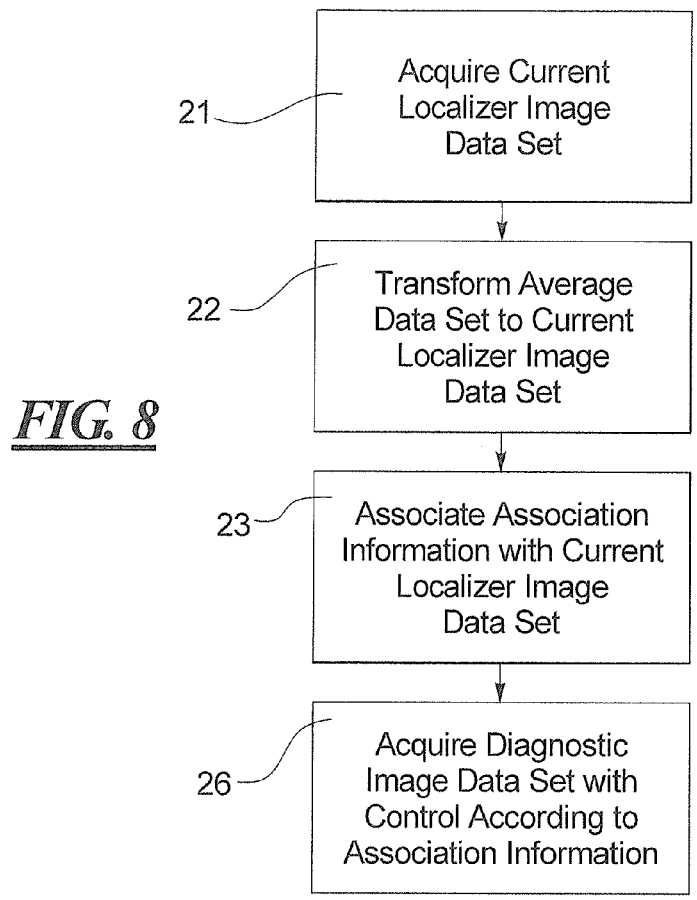
FIG. 8 is a flowchart for examination planning with the method according to an embodiment of the invention.

FIG. 8 shows how the statistical atlas can be used within the scope of the examination planning and the control of a magnetic resonance device.

In Step 21 a current localizer image data set is initially acquired using the same measurement protocol with which the localizer image data sets 4 forming the basis of the atlas were also acquired.

In Step 22, the statistical atlas should now be registered with the current localizer image data set, meaning that a transformation is sought of the average image data set to the current localizer image data set. This predominantly occurs again using an optimization method, for example a gradient downscaling method with adaptive interval width or the Gauss-Newton method, in which the function evaluation ensues distributed across the image in disjoint blocks.

As in the determination of the map with regard to the generation of the atlas, the sum of an affine transformation an a deformation transformation is viewed as a transformation. A greyscale value transformation is also additionally taken into account. The transformation parameters are sought that generate the greyscale value distribution and the deformation field which, together with the affine transformation, map the atlas as exactly as possible to the current localizer image data set. Here a degree of similarity is minimized as a cost function, meaning for example the Gaussian distance under consideration of the average image data set as well a the variances of the single pixel.

According to the invention, for the individual optimization steps it is provided according to the invention to use the previously determined primary components for the deformations and the greyscale value distribution, wherein their number is reduced to 20 for the deformation transformation and to 10 for the greyscale value transformation with sorting according to highest eigenvalues. The calculation of the gradients ensues numerically via symmetrical differences. The interval width for the calculation is individually selected for each parameter, wherein the interval width for the affine parameters and the deformation parameters is predetermined so that an image data point is displaced by a maximum of the dimension of one voxel. For the greyscale value parameters, the maximum number of greyscale values in an interval width of 15% is predetermined as a maximum. The eigenvalues previously determined in the Steps 16 and 20 are used in order to establish the maximum limits for the total deformation and the total greyscale value shift so that the triple variance should not be exceeded.

It is naturally also possible to determine the interval widths using other parameters, as this has been shown already in the preamble of the general specification.

The result of the optimization method implemented in Step 22 is a transformation that associates at least one image data point in the current localizer image data set with each image data point of the average image data set.

Figure 9:
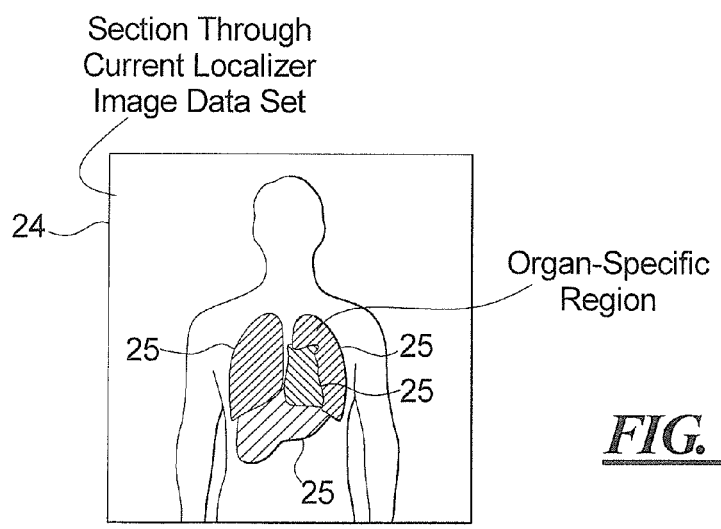
FIG. 9 shows an example of a labeled image data set.

In Step 23 it is now provided to also associate association information associated with the image data points in the average image data set with the image data points of the current localizer image data set that are currently associated with said image data points in the average image data set via the transformation, such that which structure or which organ they belong to is also known for the image data points of the current localizer image data set. The current localizer image data set is therefore labeled. One of the drawings explaining this in FIG. 9. In the section 24 there through a current localizer image data set, specific regions 25 are labeled as associated with specific organs or structures of the anatomy by the association information.

From this association information it is now possible to obtain position information and the like about the regions that are actually of interest for the current examination. In Step 26 the image acquisition and possibly also the image evaluation are thus now controlled while taking into account the association information of the current localizer image data set. It is thereby possible in a fully automatic manner to establish slices and measurement protocols and, in the ideal case, to adapt all parameters specific to the patient, in particular also with regard to the size and additional information that can be concluded from the localizer image data set. The image evaluation can also be additionally automated under consideration of the association information in that, for example, the labeling can serve as a pre-segmentation, i.e. as an initialization of a clinical segmentation, or association correspondences are established. Many possibilities are conceivable.

In the presented exemplary embodiment of the method according to the invention, it is particularly advantageously provided that all calculation steps pertaining to the image data and ensuing in Step 22 are implemented in programmable shaders of a GPU of a graphics card, wherein the texture memory of the graphics card is also used. This is explained in detail by FIG. 10. The dashed border 27 marks the region of the GPU; the dashed region 28 marks that of the CPU. Only the components of the algorithm pertaining to an optimization (represented by the box 29) run on the CPU. All operations conducted on image data run in parallel utilizing the texture memory and the excellent floating point computation resources optimized for such applications on the GPU, which is achieved via a corresponding implementation on programmable shaders. In particular the generation of, for example, deformation fields is thereby also likewise transferred to the graphics card (box 30), i.e. the multiplication of the primary components with the weighting parameters as well as the greyscale value distribution. The comparison of the images (box 31) and the calculation of the degree of similarity (box 32) occur by means of fragment shaders on the graphics card.

The upload, symbolized by the arrow 33, is thus limited to a minimum of a few scalar values (affine parameters, weighting parameters for the deformation and the greyscale value distribution); the download, represented by the arrow 34, is limited to the results (consequently the degree of similarity).

Extremely fast run times are achieved in this way; in particular an improvement by a factor of 500 was determined relative to the implementation on a CPU alone.

Figure 10:
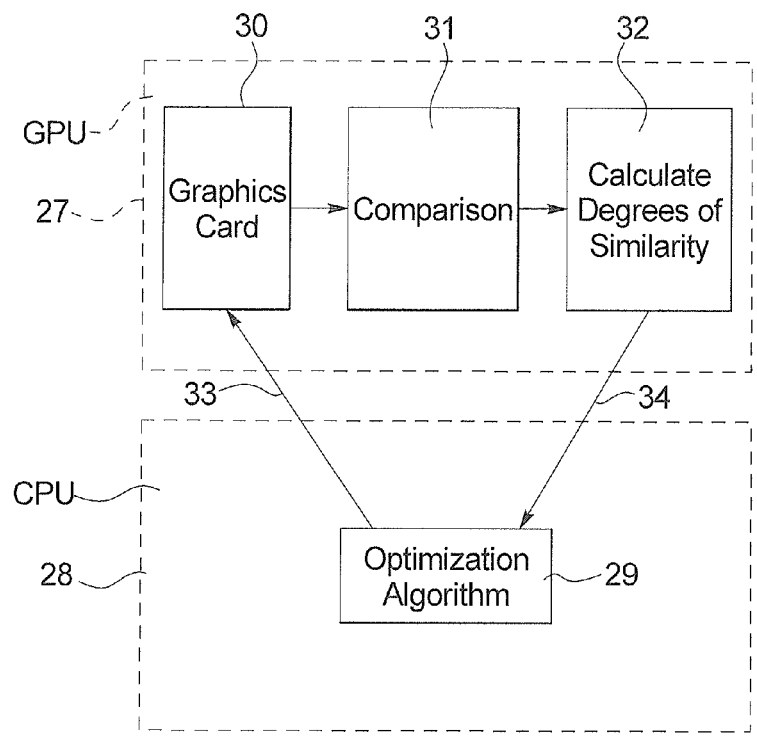
FIG. 10 is a basic illustration for implementation of method portions on a GPU of a graphics card.
Figure 11:
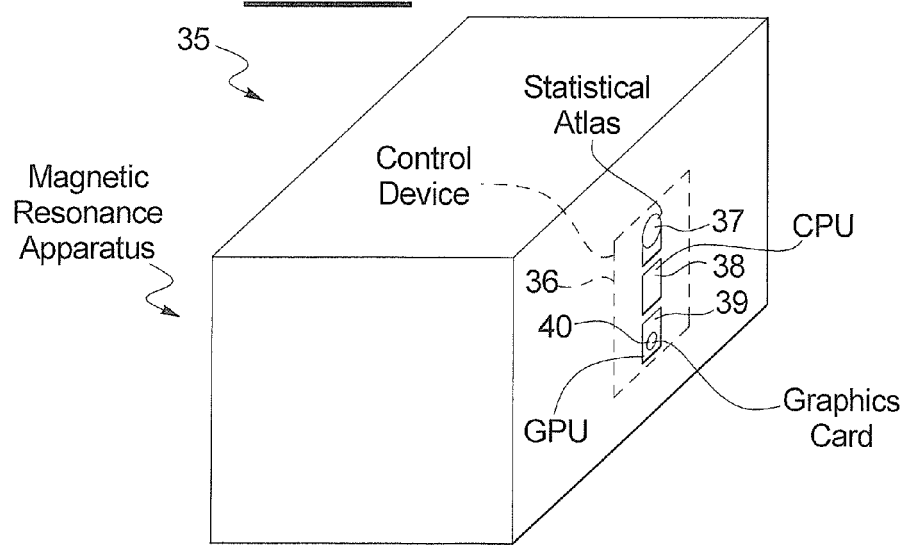
FIG. 11 schematically illustrates a magnetic resonance device according to the invention.

FIG. 11 shows a magnetic resonance apparatus 35 according to the invention. This has a control device 36 that is fashioned to implement the method according to the invention. The statistical atlas (schematically represented by 37) is in particular stored in the control device 36. The control device 36 additionally has a CPU 38 as well as a graphics card 39 with a GPU 40 with multiple programmable shaders, wherein parts of the method according to the invention have been implemented on the GPU 40, as is shown in FIG. 10.

Although modifications and changes may be suggested by those skilled in the art, it is the intention of the inventors to embody within the patent warranted hereon all changes and modifications as reasonably and properly come within the scope of his or her contribution to the art.

We claim as our invention:

1. A method for controlling acquisition of a diagnostic medical image in a medical image acquisition device, comprising the steps of:
    generating a statistical atlas for at least one part of the human body comprising a plurality of different, individual anatomical entities by compiling an average image data set from a plurality of planning image data sets respectively acquired using a specified measurement protocol to operate a medical image acquisition device, said planning image data sets each having an image control that is insufficient for making a medical diagnosis, selecting one planning image data set in said plurality of planning image data sets for use as a reference image data set, mapping all other planning image data sets in said plurality of planning imaged data sets to said reference image data set using an affine map combined with a deformation map, thereby obtaining mapped planning image data sets, averaging said mapped planning image data sets to form said average image data set, and transforming said average image data set with an inverse average map formed by averaging all maps used to generate said mapped planning image data sets;
    electronically storing the statistical atlas in a storage medium together with association information that individually labels the different anatomical entities of the human body represented by the average image data set;
    after generating and storing said statistical atlas, acquiring a current planning image data set of an examination subject in said medical image acquisition device, also using said specified image protocol or an image protocol having a contrast corresponding to a contrast of said specified image protocol;
    in a processor, accessing said statistical atlas from said storage medium and transforming the average image data set therein into the current planning image data set and thereby also causing said association information to be correctly associated with corresponding different anatomical entities said current planning image data set; and
    in said processor, generating control signals using the association information now associated with the current planning imaged data set having a control signal form for controlling acquisition of a diagnostic medical image that includes at least one of the different anatomical entities of the examination subject in said medical image acquisition device, and emitting said control signals at an output of said processor.

2. A method as claimed in claim 1 comprising generating said statistical atlas by transforming the respective planning image data sets in said plurality of planning image data sets into a common coordinate system and then averaging said plurality of planning image data sets in said common coordinate system to generate said average image data set.

3. A method as claimed in claim 1 comprising representing said deformation map as a vector field grid.

4. A method as claimed in claim 3 comprising combining said vector field grid with said affine maps using a B-spline tensor of the third order.

5. A method as claimed in claim 3 comprising implementing respective mappings of said other planning image data sets with said reference data set hierarchically, by increasing a resolution of said vector field grid incrementally in steps.

6. A method as claimed in claim 1 comprising also generating a covariance of said map in addition to said average map.

7. A method as claimed in claim 6 wherein said covariance contains affine portions, and comprising removing said affine portions from said covariance by a primary component analysis, and thereafter determining an average deformation and eigenvalues of primary components of said average deformation.

8. A method as claimed in claim 7 comprising employing at least some of the eigenvalues of the primary components to determine said deformation map.

9. A method as claimed in claim 6 comprising determining linear coefficients for said deformation map dependent on said eigenvalues of said primary components.

10. A method as claimed in claim 1 wherein each planning image data set in said plurality of planning image data sets has a grey scale value distribution, and generating said average image data set as an average of the respective grey scale value distributions of the plurality of planning image data sets, and also generating a grey scale value of covariance as said association information.

11. A method as claimed in claim 10 comprising mapping said other planning imaged data sets to said reference image data set using an affine map combined with a deformation map, and wherein said covariance comprises affine portions, and comprising removing said affine portions from said covariance by a primary component analysis and determining an average deformation and eigenvalues of primary components of said average deformation as the grey scale covariance.

12. A method as claimed in claim 11 comprising determining at least a portion of the primary components of the grey scale covariance using respective magnitudes of the eigenvalues.

13. A method as claimed in claim 11 comprising determining linear coefficients for said deformation using said eigenvalues.

14. A method as claimed in claim 1 comprising determining said affine map and said deformation map using an optimization method.

15. A method as claimed in claim 14 comprising employing a cost function is said optimization method, and formulating said cost function using an input selected from the group consisting of normalized mutual information, smoothness of a deformation vector field, and correspondence quality of designated anatomical landmarks.

16. A method as claimed in claim 1 comprising mapping said other planning image data sets to said reference image data set hierarchically by increasing a resolution of a planning image data set being mapped by stepped incrementation using a Gaussian pyramid.

17. A method as claimed in claim 1 comprising associating said association information with said average image data set by image segmentation.

18. A method as claimed in claim 1 comprising transforming said current planning image data set using an optimization method.

19. A method as claimed in claim 18 comprising employing an optimization method selected from the group consisting of a downscaling method employing an adaptive interval width, and a Gauss-Newton method.

20. A method as claimed in claim 18 comprising employing a cost function in said optimization method formulated as a sum of squares of distance.

21. A method as claimed in claim 1 comprising in said processor, determining, for said current planning image data set, a position of a region of interest to be acquired in said diagnostic image using said association information, and controlling said medical image acquisition device to require said diagnostic medical image so as to encompass said region of interest.

22. A method as claimed in claim 1 comprising, in a computerized evaluation device, automatically evaluating said diagnostic medical image dependent on said association information associated with said current planning image data set.

23. A method as claimed in claim 1 comprising providing said processor with a graphics card, and implementing at least a portion of said transformation on said graphics card.

24. A method as claimed in claim 23 comprising implementing all of said calculations on said graphics card.

25. A method as claimed in claim 23 comprising implementing said transformation in a graphics processing unit comprising multiple programmable shaders.

26. A method as claimed in claim 1 comprising employing a magnetic resonance imaging device as said image acquisition device, and using localizer image data sets as said plurality of planning image data sets and as said current planning image data set.

27. A method as claimed in claim 1 comprising employing a computed tomography apparatus as said image acquisition device, and employing low radiation-dose image data sets as said plurality of planning image data sets and as said current planning image data set.

28. A medical image acquisition system comprising:

a processor configured to generate a statistical atlas for at least one part of the human body, said statistical atlas comprising a plurality of different, individual anatomical entities, said processor being configured to generate said statistical atlas by compiling an average image data set from a plurality of planning image data sets respectively acquired using a specified measurement protocol to operate a medical image acquisition device, said planning image data sets each having an image control that is insufficient for making a medical diagnosis, selecting one planning image data set in said plurality of planning image data sets for use as a reference image data set, mapping all other planning image data sets in said plurality of planning imaged data sets to said reference image data set, thereby obtaining mapped planning image data sets, averaging said mapped planning image data sets to form said average image data set, and transforming said average image data set with an inverse average map formed by averaging all maps used to generate said mapped planning image data sets, and said processor being configured to also generate association information that individually labels the different anatomical entities of the human body represented by the average image data set;

a storage medium;

said processor being configured to store said statistical atlas together with said association information;

a medical image data acquisition device that acquires a current planning image data set of an examination subject in said medical image acquisition device, also using said specified image protocol or an image protocol having a contrast corresponding to a contrast of said specified image protocol;

said processor being configured to access said statistical atlas from said storage medium and to transform the average image data set therein into the current planning image data set and thereby also cause said association information to be correctly associated corresponding different anatomical entities with said current planning image data set;

said processor being configured to generate control signals using the association information now associated with the current planning image data set, and having a control signal form for controlling acquisition of a diagnostic medical image that includes at least one of the different anatomical entities of the examination subject in said medical image acquisition device, and to emit said control signals at an output of said processor; and said medical image data acquisition device being configured to receive said control signals from said processor and to operate to acquire said diagnostic medical image according to said control signals.

29. A method as claimed in claim 1 comprising supplying said control signals from said processor to said medical image acquisition device, and operating said medical image acquisition device according to said control signals to acquire said diagnostic medical image.

* * * * *